US005644129A

United States Patent [19]
Hsu et al.

[11] Patent Number: 5,644,129
[45] Date of Patent: Jul. 1, 1997

[54] DIRECT ANALYSIS OF PARAFFIN AND NAPHTHENE TYPES IN HYDROCARBON

[75] Inventors: Chang S. Hsu, Bridgewater; Saul C. Blum, Edison; Zhenmin Liang, Branchburg; Peter B. Grosshans, Whitehouse Station; Winston K. Robbins, New Providence, all of N.J.

[73] Assignee: Exxon Research & Engineering Company, Florham Park, N.J.

[21] Appl. No.: 595,681

[22] Filed: Feb. 2, 1996

[51] Int. Cl.$^6$ .............................. B01D 59/44; H01J 49/00
[52] U.S. Cl. .......................................... 250/282; 250/423 F
[58] Field of Search ..................................... 250/282, 288, 250/288 A, 423 F

[56] References Cited

U.S. PATENT DOCUMENTS

| | | | |
|---|---|---|---|
| 4,170,543 | 10/1979 | Lipscomb et al. | 208/14 |
| 4,888,482 | 12/1989 | Kato | 250/423 F |

Primary Examiner—Bruce Anderson
Attorney, Agent, or Firm—Ronald D. Hantman

[57] ABSTRACT

The present invention is a method to distinguish and measure normal paraffins, isoparaffins, and naphthenes in a saturated hydrocarbon mixture. The method includes the step of field-ionizing hydrocarbon mixture; separating the normal paraffins, isoparaffins and naphthenes as a separate saturates class; and detecting the normal paraffins as molecular ions, naphthenes as molecular ions, and isoparaffins as fragment ions.

11 Claims, 5 Drawing Sheets

DIRECT ANALYSIS OF PARAFFIN AND NAPHTHENE TYPES IN HYDROCARBON

BACKGROUND OF THE PRESENT INVENTION

Normal paraffins, isoparaffins, and naphthenes, by number of rings, can be distinguished and measured in saturated hydrocarbon mixtures by a single mass spectrometric analysis. The saturates fraction can be obtained off-line by open-column or preparative liquid chromatography (LC) separations. In a preferred embodiment of this invention, this fraction is separated from the rest of the hydrocarbon mixture by LC on-line to a mass spectrometer via interfaces such as the moving belt or particle beam. Using field ionization (FI), the normal paraffins and naphthene ring types present are primarily detected as molecular ions whereas the isoparaffins are predominantly detected as characteristic fragment ions. By measuring the sensitivities of model hydrocarbon compounds representative of the various types, we are able to determine the distribution of saturate hydrocarbon types; in addition, the carbon number distribution within each type can be measured from the detected molecular ions.

Prior art determines the weight percentages of the total paraffins and naphthenes (1- to 6-rings) in a pre-separated (as discussed above) saturates fraction using high voltage (50–100 eV) electron-impact ionization (EI) mass spectrometry. "1994 Annual Book of ASTM Standards," Volume 05.02, ASTM method D2786-86. The percentage of normal paraffins is then determined by either of two methods: 1) gravimetrically by extraction of normal paraffins (molecular sieve or urea adduction) or 2) chromatographically using gas chromatography (GC). Isoparaffins are then calculated by difference between total and normal paraffins. W. L. Mead, *Anal. Chem.*, 40, 743–747 (1968).

Field ionization has two major advantages over the prior art: a single mass spectrometric measurement provides (1) the concentrations of normal paraffins and isoparaffins as well as naphthenes and (2) the carbon number distributions within individual compound types. The pre-separated saturates fraction can be introduced by any of several inlet systems commonly employed, i.e., batch, GC, supercritical fluid chromatography, etc. The preferred embodiment of this invention offers additional advantages related to on-line separation of saturates from complex hydrocarbon mixtures: only require very small sample size, no need of time-consuming pre-separation, and enhanced chromatographic resolution. Prior art uses pre-separation and several analyses lend greater uncertainty to the accuracy of the measurements. Other advantages may include greater accuracy and selectivity.

This methodology is particularly effective for hydrocarbon mixtures boiling above 300° F., preferably in the 650°–1050° F. range. This invention is therefore useful to characterize hydrocarbon streams where knowledge of saturates composition is important such as in catalytic cracking, lube processing, biodegradability, and diesel fuel blending, crude oil production and transport through pipeline, among other processes and products. This invention provides molecular-level characterization, by carbon number distribution, of the saturated hydrocarbon classes, thereby enabling enhanced understanding of the relationship between structure and product properties, performance, and processability in these key areas.

The distinction between and measurement of saturated hydrocarbon classes in heavy petroleum oils (with boiling points greater than 650° F.) are valuable in understanding conversions and selectivities in refining processes such as catalytic cracking and lube processing. It also has value in assessing the origins of oil because several hydrocarbon types within these classes are biological markers of the oil precursors. The ability to achieve such measurements in a single analysis would improve the reliability of the measurements and facilitate process optimization using a molecular basis. In contrast, similar results from a combination of techniques applied to different sample aliquots would increase the uncertainty of the data so derived.

SUMMARY OF THE INVENTION

The present invention is a method to distinguish and measure normal paraffins, isoparaffins, and naphthenes in a saturated hydrocarbon mixture. The method includes the step of field-ionizing hydrocarbon mixture; separating the normal paraffins, isoparaffins and naphthenes as a saturates class; and detecting the normal paraffins as molecular ions, naphthenes as molecular ions, and isoparaffins as fragment ions.

DESCRIPTION OF THE PREFERRED EMBODIMENT

The distributions of normal paraffins, isoparaffins and naphthenes in a heavy petroleum saturates fraction, such as of a lubricant oil basestock affect many properties of the oil, such as pour point, cloud point, etc. Prior art uses mass spectrometry to determine the distribution of normal and isoparaffins and naphthenes, and gas chromatography to determine the split between normal and isoparaffins. This combination of gas chromatography and mass spectrometry suffers several draw-backs. To quantify normal paraffins by gas chromatography, baselines must be defined for the normal paraffin peaks over the envelope that constitutes the isoparaffins and naphthenes. The baseline becomes difficult to define when normal paraffins are not major components in a hydrocarbon mixture. Coelution of other hydrocarbon types with the normal paraffins is another difficulty that is frequently encountered.

The MS measurement of paraffin and naphthene types in mixtures of saturated hydrocarbons is conventionally performed by high voltage (70 volts) electron ionization (EI) on the basis of fragment ion intensities. These measurements use pre-calibrated "inverse sensitivity matrices" which are established based on two factors: (1) average carbon number estimated from the distribution of the molecular ions of normal paraffins and (2) the normal/isoparaffin ratio estimated from the ratio of molecular to fragment ion intensities. Because field ionization (FI) is reported to produce predominantly molecular ions of various saturates types under a variety of experimental conditions, we investigated FI for the quantitative characterization of saturates fractions.

We have invented an analytical method of using field ionization mass spectrometry to quantify normal and isoparaffins and 1- to 6-ring naphthenes directly in hydrocarbon oils (i.e., no other analytical methods are necessary). In addition, naphthenes can be measured more accurately than with the prior art of type analysis using EI because, to first order, only one series of ions, molecular ions except in the case of isoparaffins, are used to represent each component. The normal/isoparaffin split is obtained indirectly from the alkyl fragment ions which are the most intense peaks in the FI spectra of isoparaffins. This invention has many business applications where saturate composition is essential, such as catalytic cracking, lube processing, etc. This invention enables the determination of the levels of naphthenes, normal paraffins, and isoparaffins with a single MS analysis either with an on-line LC separation or with an off-line separation of the saturates fraction. We have been successful in implementing this method by re-configurating a commercial field ionization source to accommodate the moving belt interface for on-line liquid chromatography-mass spectrometric measurements (See Examples).

Optimization of FI Conditions for Quantitative Analysis

An important part of the present invention is the empirical determination of the experimental conditions which enable the quantitative measurements described herein. The parameters that require adjustment are as follows:

1. Scan-In-Progress Current (SIP): the current through the FI emitter during the mass scans.
2. Between Scan Flash Current (Flash): the current through the FI emitter between mass scans.
3. Scan Speed: the rate at which the mass range is scanned.
4. Mass Range: the range of mass-to-charge values that are measured.
5. Interscan Delay: the time between the end of one mass scan and the beginning of the next mass scan.
6. Temperatures: the source temperature as well as the temperatures of the various regions through which the analyte molecules pass between the sample introduction system (LC interface, GC interface, or batch inlet system) and the source. In general, there are several heaters which control the temperatures of the various regions independently.

Using a blend of normal paraffins (or another homologous series) with a molecular weight distribution (MWD) similar to that of the sample, the MWD of the blend is measured by GC-FID. The FI parameters listed above are varied in successive FI/MS experiments until a set of conditions is found which yields an apparent MWD that reasonably approximates that found in the GC-FID measurements. These conditions are then used for the FI/MS analysis of the sample(s).

EXAMPLE 1

Figure 1:
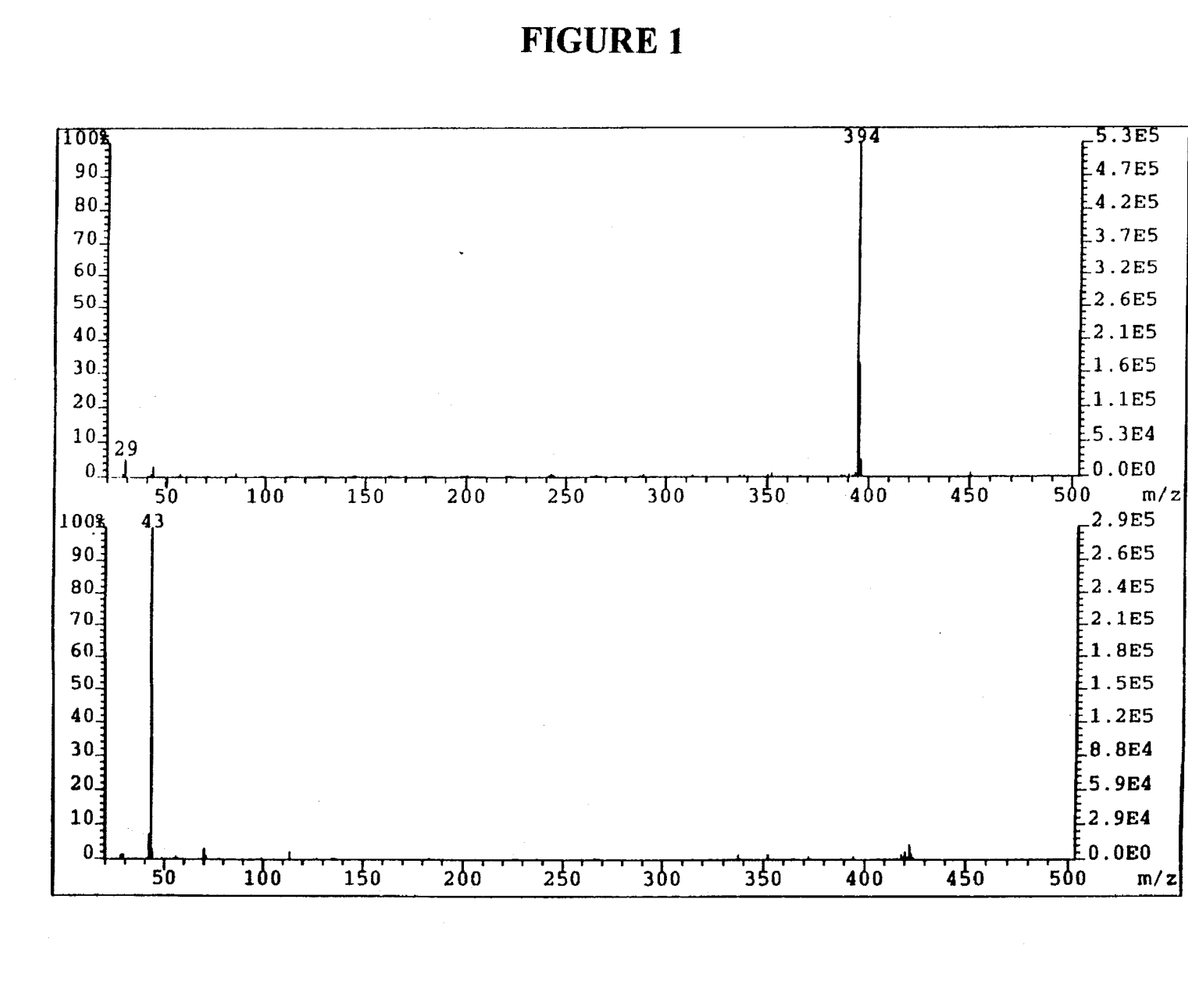
FIG. 1 shows the mass spectra of n-octacosane (top) and squalane (bottom).
Figure 2:
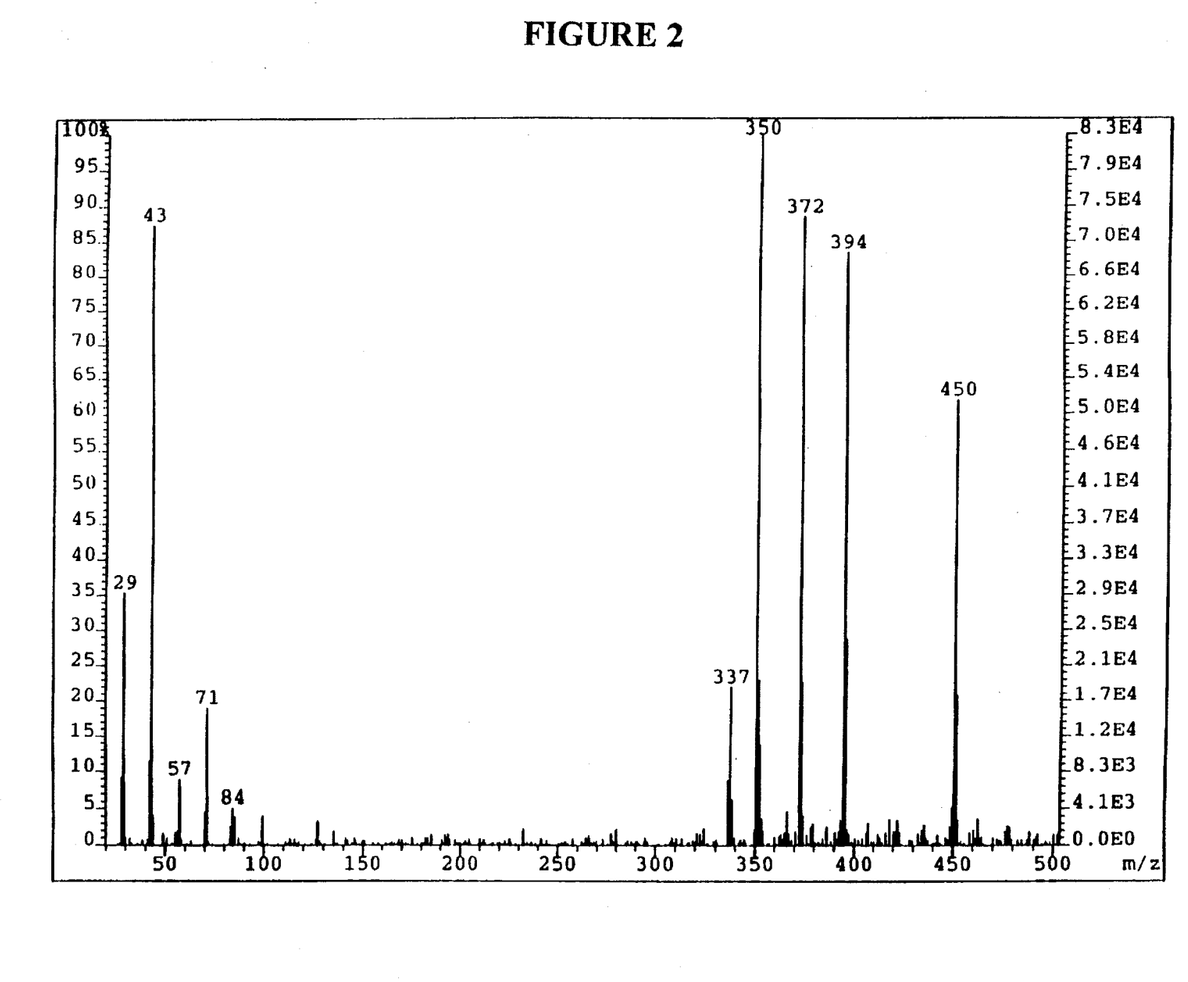
FIG. 2 shows the mass spectrum of a mixture of n-dotriacontane, n-octacosane 3-ethyltetracosane, squalane, cholestane, and nonadecylcyclohexane.

Our analytical method is based on a discovery of different fragmentation characteristics of normal paraffins, isoparaffins and naphthenes under FI conditions that were optimized for quantitative analysis. A mixture of six compounds representative of normal and isoparaffin and naphthene types, n-dotriacontane, n-octacosane, 3-ethyltetracosane, squalane, cholestane, and n-nonadecylcyclohexane, was used. Under conditions optimized for normal paraffins (200° C. source temperature, 20 mA scan-in-progress (SIP) current and 30 mA flash current), the molar sensitivities of normal paraffins and naphthenes are nearly equal (Table 1). However, isoparaffins undergo significant fragmentation which results in more than an order of magnitude reduction in sensitivity when only molecular ions are considered in the calculation. This is illustrated by the mass spectra in FIG. 1 of a normal paraffin, n-octacosane, and an isoparaffin, squalane (2,6,10, 15,19,23-hexamethyl tetracosane). FIG. 2 shows how the spectrum from the mixture of the above six compounds contains molecular ions from the normal paraffins and naphthenes and alkyl fragment ions between mass 10 to 200, mainly from the isoparaffins.

Based on the data in Table 1, we assume that the molar sensitivities of normal paraffins and mono- and multi-ring naphthenes are all unity. Thus, we can construct an 8×8 Sensitivity matrix, S, a column vector representing the mole fractions of the 8 components (normal and isoparaffins and 1- to 6-ring naphthenes), x, and a column vector representing the sums of the de-isotoped ion intensities of the seven homologous series of molecular ions and the alkyl fragment ions. S, x, and sdi are then related as follows:

$$Sx = sdi \quad (1)$$

$$\begin{bmatrix} 1 & 0 & 0 & 0 & 0 & 0 & 0 & 0 \\ 0 & 1 & 0 & 0 & 0 & 0 & 0 & 0 \\ 0 & 0 & 1 & 0 & 0 & 0 & 0 & 0 \\ 0 & 0 & 0 & 1 & 0 & 0 & 0 & 0 \\ 0 & 0 & 0 & 0 & 1 & 0 & 0 & 0 \\ 0 & 0 & 0 & 0 & 0 & 1 & 0 & 0 \\ 0 & 0 & 0 & 0 & 0 & 0 & 1 & .05 \\ 0 & 0 & 0 & 0 & 0 & 0 & .10 & .59 \end{bmatrix} \begin{bmatrix} x(1-r) \\ x(2-r) \\ x(3-r) \\ x(4-r) \\ x(5-r) \\ x(6-r) \\ x(n-P) \\ x(i-P) \end{bmatrix} = \begin{bmatrix} sdi(1-r) \\ sdi(2-r) \\ sdi(3-r) \\ sdi(4-r) \\ sdi(5-r) \\ sdi(6-r) \\ sdi(n-P) \\ sdi(Alk) \end{bmatrix} \quad (2)$$

The elements of S, $S_{ij}$, are taken from Table 1 assuming that the molar sensitivities of normal paraffins and naphthenes are unity, an assumption which is well within experimental error for the model compounds studied under the conditions employed. The off-diagonal elements arise from the fact that normal paraffins contribute to the alkyl fragment ion intensities and that the FI spectra of isoparaffins do show small amounts of molecular ions. The contribution of the normal paraffins to the sum of alkyl ion intensities has been determined to be 15% of the sum of molecular ion intensities for a sample of Polywax 500; thus, the value of the corresponding element in S is the average of 0.15 and the value found for the two model compounds in Table 1(0.05). It is unclear why the molar sensitivities of isoparaffins are lower than those of the other compounds that were studied; however, some of the "missing" ion intensity may be at m/z=15 as the magnet scan terminated at m/z=20. More detailed studies of saturate sensitivities are planned to make the matrix, S, more exact.

Now, the sum of de-isotoped ion intensities column vector, sdi, can be obtained by well-known transformation methods, including those used in ASTM D2786 et al., from the average mass spectrum obtained under the LC-FI/MS conditions described previously. Multiplying this vector by the inverse of matrix S, $S^{-1}$, and renormalizing we obtain the mole fraction vector, x.:

$$s^{-1} sdi(1 - r)sdi = x \quad (4)$$

where $$S^{-1} \cong \begin{bmatrix} 1 & 0 & 0 & 0 & 0 & 0 & 0 & 0 \\ 0 & 1 & 0 & 0 & 0 & 0 & 0 & 0 \\ 0 & 0 & 1 & 0 & 0 & 0 & 0 & 0 \\ 0 & 0 & 0 & 1 & 0 & 0 & 0 & 0 \\ 0 & 0 & 0 & 0 & 1 & 0 & 0 & 0 \\ 0 & 0 & 0 & 0 & 0 & 1 & 0 & 0 \\ 0 & 0 & 0 & 0 & 0 & 0 & 1.0085 & -.0855 \\ 0 & 0 & 0 & 0 & 0 & 0 & -.1709 & .7094 \end{bmatrix}$$

To an excellent approximation, the molecular weight distributions of all saturate compound types are the same for a given distillate cut. This fact, the well-known methods for generating a de-isotoped spectrum, and equations 3 and 4 allow us to perform type analysis of saturates fractions including quantitation of both normal paraffins and isoparaffins directly by MS. Iterative approaches may also be used to solve the inverse problem.

EXAMPLE 2

We have analyzed a set of lube basestock saturates samples by this technique, which include a saturates fraction, a dewaxed oil obtained from this fraction by urea adduction, and the recovered wax.

Figure 3:
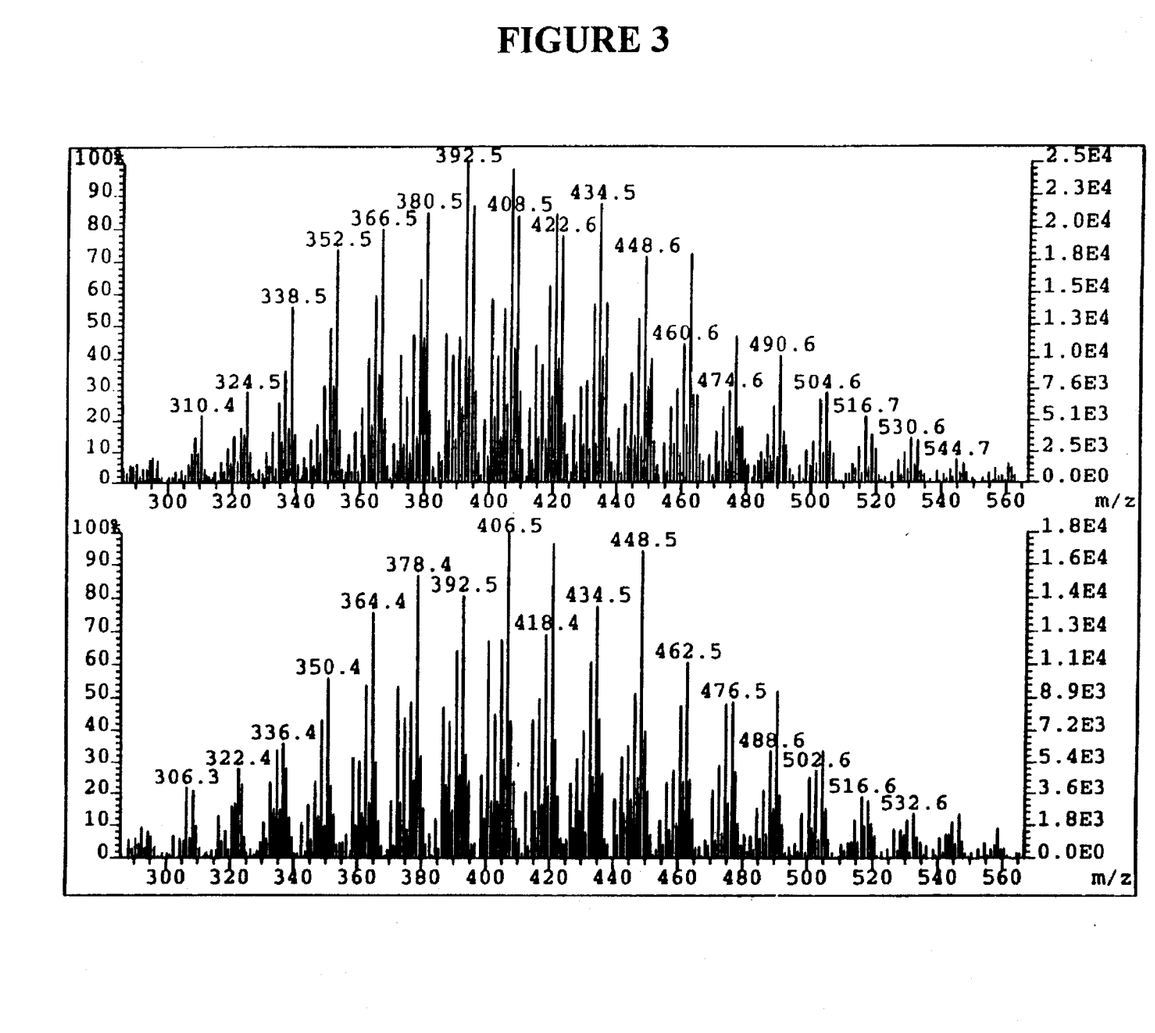
FIG. 3 shows the mass spectra of molecular ion regions of whole saturates fraction (top) and the dewaxed oil (bottom) from this saturates fraction.
Figure 4:
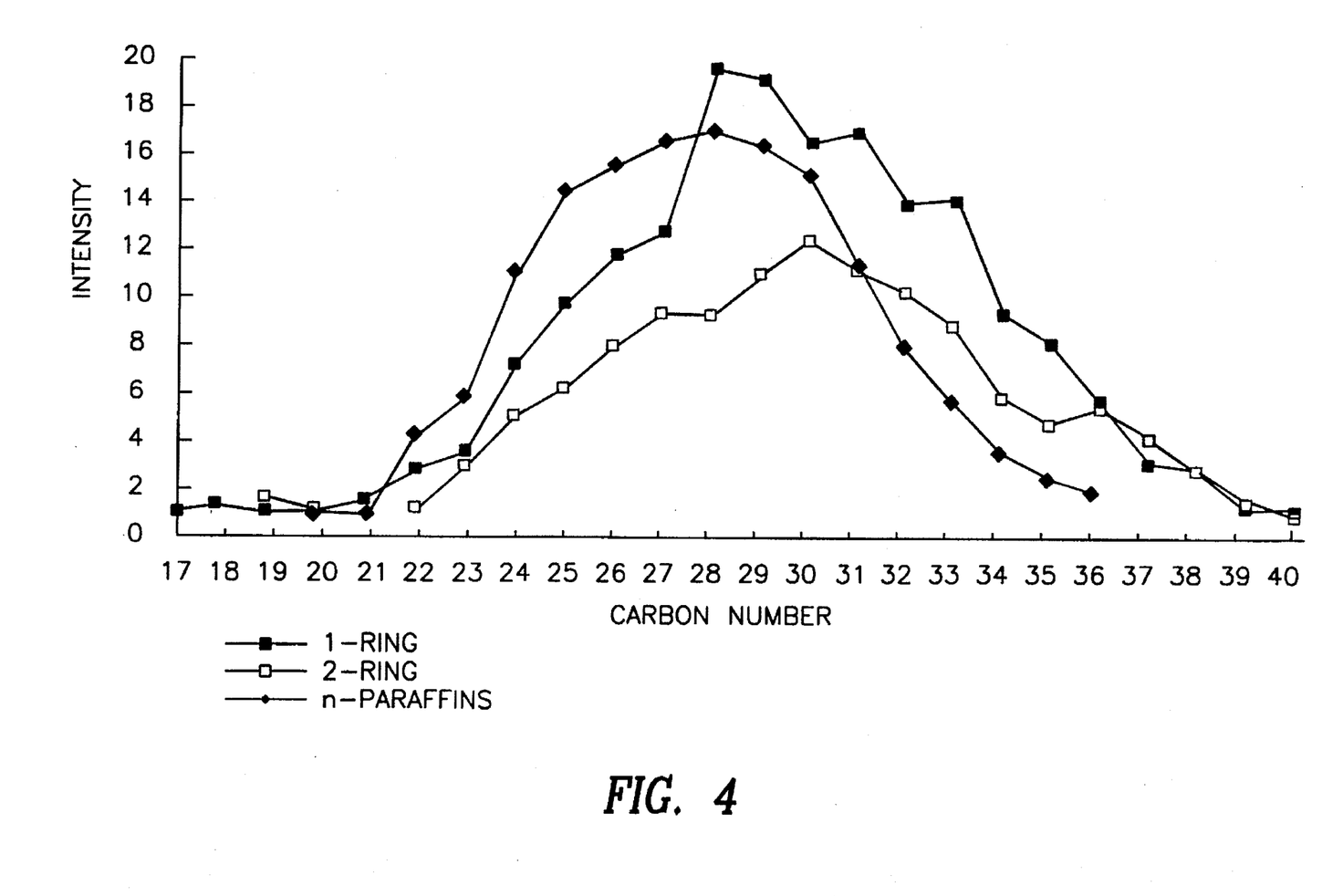
FIG. 4 shows the carbon number distribution of normal paraffins, 1-ring naphthenes, and 2-ring naphthenes in the 650°–850° F. saturates fraction.

In FIG. 3, the mass spectra of the molecular ion region of the whole saturates fraction and the dewaxed oil are shown. It can be seen that the intensities of molecular ions from paraffins in the dewaxed oil are much lower than those in the whole fraction. FIG. 4 shows carbon number distributions of three representative types, normal paraffins, 1-ring naphthenes, and 2-ring naphthenes, extracted from the mass spectrum of the whole saturates fraction. Notice that the average carbon number of the series increases with the ring number. The average carbon numbers of normal paraffins, 1-ring naphthenes shown are 27.9, 29.6 and 30.0, respectively.

Prior to this invention, no existing technique can provide accurate quantitation for all saturate compound types in a 650°–1050° F. boiling fraction of petroleum. We obtained the quantitation of normal paraffins by GC for comparison with the FI results. Table 2 lists the concentrations of normal paraffins of the separate lube basestock sample suite as measured by GC-FID and LC/FIMS. In the whole saturates fraction, GC measured 13.3% of normal paraffins, compared with 14.7% by FI. In the recovered wax, GC gave 54.0% normal paraffins while FI showed 58.2%. For these two samples, GC and FI measurements on normal paraffins are in good agreement. In the dewaxed oil, the normal paraffins measured by GC and FI are 1.0% and 3.2% respectively. The difference is probably due to the fact that for FI, the correction for isoparaffins is only accurate to ~1% absolute, whereas for GC, the measurement of small paraffin peaks on a big isoparaffins and naphthenes envelope reduces the accuracy of measurements. Overall, the comparison suggest that the normal paraffin values by FI agree with those by GC as both techniques have significant uncertainty in the determinaton of low concentrations of normal paraffins.

Figure 5:
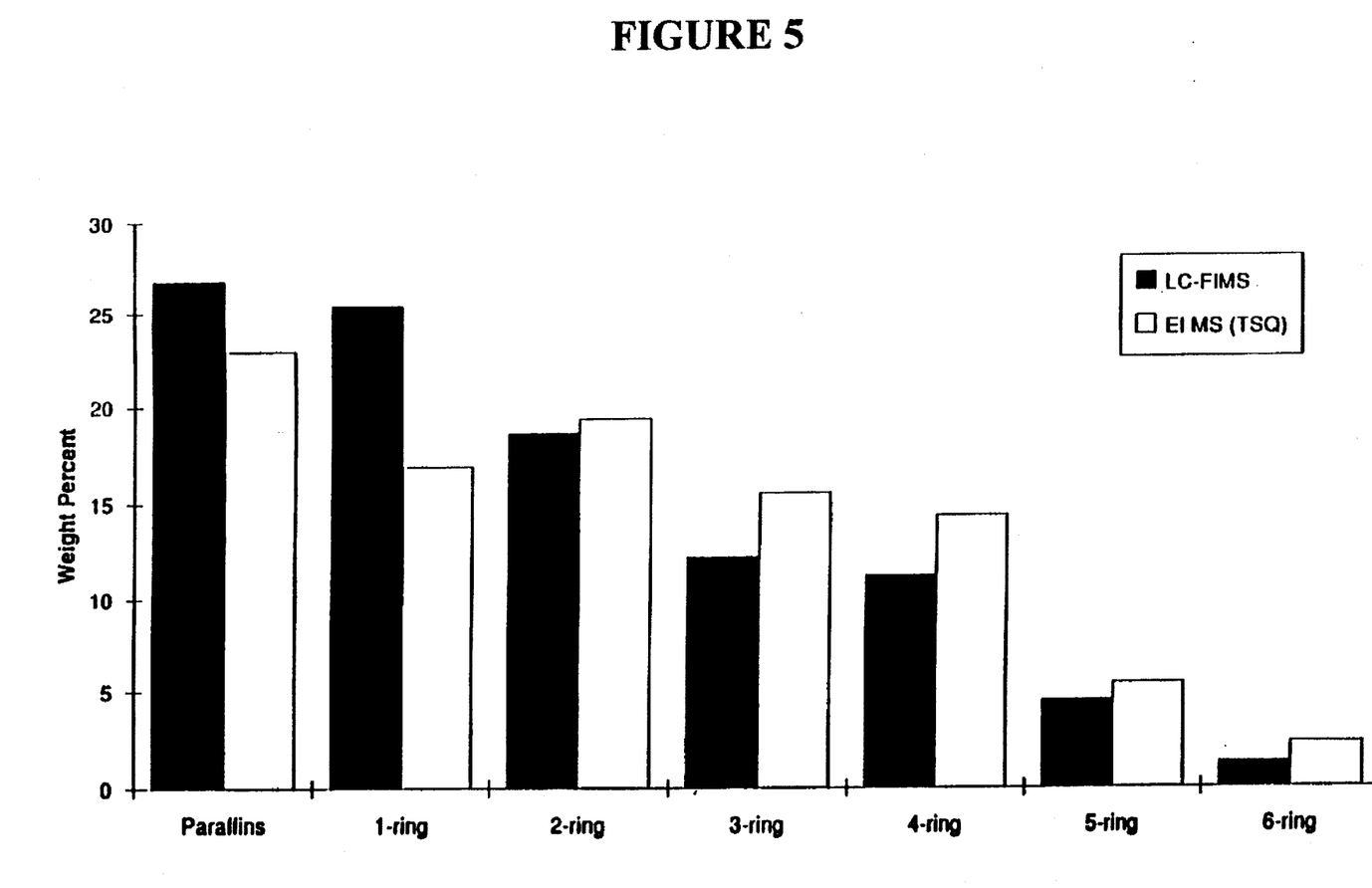
FIG. 5 shows the weight percent distributions of paraffins/naphthene types in a dewaxed oil measured by LC/FIMS and by ASTM method D2786-86 using EIMS with GC and a direct insertion probe.

We also compared the compound type distribution of a dewaxed oil obtained by FI with that by the ASTM D2786 high voltage EIMS method (FIG. 5). The values of paraffins, 2-ring, 5-ring and 6-ring naphthenes are in good agreement. The differences in the rest of the types are all within ~5% in absolute weight percentage, within the reproducibility of the ASTM method.

In order to evaluate the relative accuracy of the two methods among the types that show differences, we conducted two simple standard addition experiments. n-Nonadecyl cyclohexane and cholestane were added into the dewaxed oil in a ratio of 1 to 10 in separate standard addition experiments. The concentration of each standard compound measured by FI and EI is compared with its actual concentration to identify which technique gives better quantitative results. As suggested in Table 3, FI produces more accurate results than the ASTM EI method for these compound types.

Returning to the lube basestock suite, the FI results of the recovered wax show 58.2% normal paraffins, 24.1% isoparaffins, and 15.5% 1-ring naphthenes. The 2- to 6-ring naphthenes are basically untouched by urea-adduction; therefore, these multi-ring naphthenes can be used as internal standards for material balance. The weight distributions by FI for the whole saturates fraction, the dewaxed oil, and the recovered wax are shown in Table 4. The totals of weight percentages of multi-ring naphthenes for the whole fraction and dewaxed oil are 36.5% and 47.8% respectively. Because these multi-ring naphthenes are not removed in the dewaxing process, one can use these two numbers to calculate the amount of material recovered in the dewaxed sample. We find 100*36.5/47.8=76.4% recovered; the actual recovery rate is 74.7%. When the normalized weight percentages of 2- to 6-ring naphthenes in the dewaxed oil are multiplied by 76.4%, their values match closely with those of the whole fraction. Because the wax recovered represents 23.6% of the whole fraction, the weight percentages of paraffins and 1-ring naphthenes in the wax have been adjusted accordingly. The adjusted percentages of paraffins/naphthenes in the wax are added back to those of the dewaxed oil. Their sums agree well with the percentages of corresponding paraffin/naphthene types in the whole fraction which is a strong indication of the self-consistency and accuracy of the LC/FIMS technique.

TABLE 1

Relative molar sensitivity of six model compounds in FIMS.

| Compound | Relative Molar Sensitivity Based on Molecular Ions | Relative Molar Sensitivity Based on Alkyl Ions |
|---|---|---|
| n-dotriacontane | 1.04 ± 0.13 | 0.05* |
| n-octacosane | 1.03 ± 0.13 | 0.05* |
| 3-ethyltetracosane | 0.06 ± 0.008 | 0.51 ± 0.06 |
| squalane | 0.03 ± 0.006 | 0.59 ± 0.03 |
| cholestane | 0.99 ± 0.16 | 0 |
| n-nonadecylcyclohexane | 1.00 | 0 |

*obtained from mass spectrum of pure compound.

TABLE 2

Normal paraffin concentrations measured by GC and LC/FIMS (in weight percents)

| Sample | Normal Paraffins |
|---|---|
| Whole Saturates | |
| LC/FIMS | 14.7 |
| GC (note) | 13.3 |
| Dewaxed Oil | |
| LC/FIMS | 3.2 |
| GC (note) | 1.0 |
| Wax | |
| LC/FIMS | 58.2 |
| GC (note) | 54.0 |

Note: Normal paraffins and isoparaffins obtained by GC are peaks above the envelopes of the chromatograms.

TABLE 3

Comparison of measured and actual concentrations of standard compounds added into the dewaxed oil in the standard addition experiments (in weight percent, average of three measurements).

| Compound Added | Measured Conc. by LC/FIMS | Measured Conc. by EIMS (ASTM) | Actual Conc. |
|---|---|---|---|
| Cholestane (4-ring naphthene) | 8.0% | 18.9% | 9.6% |
| Nonadecylcyclohexane (1-ring naphthene) | 7.0% | 6.4% | 9.0% |

TABLE 4

Weight percentages of paraffin/naphthene types in the dewax sample suite.

| Sample | nP[a] | iP[a] | 1-Ring Naph | 2-Ring Naph | 3-Ring Naph | 4-Ring Naph | 5-Ring Naph | 6-Ring Naph | 2- to 6-Ring Naphthenes |
|---|---|---|---|---|---|---|---|---|---|
| Whole Fraction | 14.7 | 27.4 | 21.4 | 14.2 | 9.2 | 8.1 | 3.5 | 1.5 | 36.5 |
| Dewaxed Oil | 3.2 | 23.6 | 25.4 | 18.6 | 12.0 | 11.2 | 4.5 | 1.3 | 47.8 |
| Dewaxed Oil (Adjusted)[b] | 2.4 | 18.0 | 19.4 | 14.2 | 9.3 | 8.6 | 3.4 | 1.0 | 36.5 |
| Wax (Adjusted)[c] | 13.8 | 5.7 | 3.7 | 0.5 | 0 | 0 | 0 | 0 | — |
| Dewaxed Oil + Wax (Adjusted)[d] | 16.2 | 23.7 | 23.1 | 14.7 | 9.3 | 8.6 | 3.4 | 1.0 | 37.0 |

Notes:
[a] nP = normal paraffins and iP = isoparaffins.
[b] The adjusted values of the dewaxed oil are the normalized values multiplied by 0.764 (recovery rate, see text).
[c] The adjusted values of the recovered wax are the normalized values multiplied by 0.236 (the weight percent that removed as wax from the saturates fraction).
[d] The sum of the adjusted percentages of the dewaxed oil and the recovered wax for material balance.

What is claimed is:

1. A method to distinguish and measure normal paraffins, isoparaffins, and naphthenes in a saturated hydrocarbon mixture comprising:

(a) field-ionizing said hydrocarbon mixture, (b) separating said normal paraffins, isoparaffins, and naphthenes, and (c) detecting said normal paraffins as molecular ions, naphthenes as molecular ions, and isoparaffins as fragment ions.

2. The method of claim 1 further comprising the step of determining the ion abundances of said normal paraffins, isoparaffins, and naphthenes.

3. The method of claim 2 wherein said naphthenes are 1 to 6-ring naphthenes.

4. The method of claim 2 wherein said saturates hydrocarbon mixture has a boiling point within the range 650° F. and 1050° F.

5. The method of claim 2 further comprising the step of determining the weight percentages of said normal paraffins, isoparaffins and naphthenes from said ion abundances.

6. The method of claim 1 wherein said saturates hydrocarbon mixture has an initial boiling point above 300° F.

7. The method of claim 1 further comprising an initial step of obtaining said saturates hydrocarbon mixture is obtained by liquid chromatography separations.

8. The method of claim 7 wherein said liquid chromatography is off-line, e.g., open column.

9. The method of claim 7 wherein said liquid chromatography is on-line.

10. The method of claim 1 further comprising the step of determining the carbon number of said normal paraffins and said naphthenes.

11. The method of claim 1 wherein said fragment ions have a mass to charge ratio of 10 to the highest molecular mass of the components in the mixture, preferably 10–200 daltons.

* * * * *